United States Patent [19]

Thal

[11] Patent Number: 5,720,765
[45] Date of Patent: Feb. 24, 1998

[54] KNOTLESS SUTURE ANCHOR ASSEMBLY

[76] Inventor: Raymond Thal, 11321 Bright Pond La., Reston, Va. 22094

[21] Appl. No.: 551,648

[22] Filed: Nov. 1, 1995

Related U.S. Application Data

[63] Continuation-in-part of Ser. No. 471,508, Jun. 6, 1995, Pat. No. 5,569,306.
[51] Int. Cl.⁶ .................................................. A61B 17/00
[52] U.S. Cl. ........................ 606/232; 606/73; 606/75; 24/358; 24/706.3; 24/711.4; 24/711.5
[58] Field of Search .................... 606/232, 75, 73, 606/213, 148, 139; 24/357, 358, 360, 362, 706.2, 706.3, 707.9, 708, 711.4, 711.5

[56] References Cited

U.S. PATENT DOCUMENTS

| | | |
|---|---|---|
| 4,007,743 | 2/1977 | Blake . |
| 4,532,926 | 8/1985 | O'Holla . |
| 4,537,185 | 8/1985 | Stednitz . |
| 4,632,101 | 12/1986 | Freedland . |
| 4,721,103 | 1/1988 | Freedland . |
| 4,741,330 | 5/1988 | Hayhurst ................................ 606/232 |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,224,946 | 7/1993 | Hayhurst et al. . |
| 5,236,438 | 8/1993 | Wilk ........................................ 606/216 |
| 5,236,445 | 8/1993 | Hayhurst et al. . |
| 5,258,016 | 11/1993 | DiPoto et al. . |
| 5,306,290 | 4/1994 | Martins et al. ....................... 606/232 |
| 5,318,578 | 6/1994 | Hasson ................................... 606/232 |
| 5,356,413 | 10/1994 | Martins et al. . |
| 5,358,511 | 10/1994 | Gatturna et al. . |
| 5,370,661 | 12/1994 | Branch . |
| 5,370,662 | 12/1994 | Stone et al. . |
| 5,372,146 | 12/1994 | Branch . |
| 5,372,599 | 12/1994 | Martins . |
| 5,383,905 | 1/1995 | Golds et al. . |
| 5,400,805 | 3/1995 | Warren . |
| 5,500,000 | 3/1996 | Feagin et al. ......................... 606/232 |
| 5,545,180 | 8/1996 | Le et al. ................................. 606/232 |

*Primary Examiner*—Jeffrey A. Schmidt
*Attorney, Agent, or Firm*—Hoffman, Wasson & Gitler

[57] ABSTRACT

A one-piece or two-piece knotless suture anchor assembly for the attachment or reattachment or repair of tissue to a bone mass. The assembly allows for an endoscopic or open surgical procedure to take place without the requirement of tying a knot for reattachment of tissue to bone mass. In one embodiment, a spike member is inserted through tissue and then inserted into a dowel-like hollow anchoring sleeve which has been inserted into a bone mass. The spike member is securely fastened or attached to the anchoring sleeve with a ratcheting mechanism thereby pulling or adhering (attaching) the tissue to the bone mass.

14 Claims, 6 Drawing Sheets

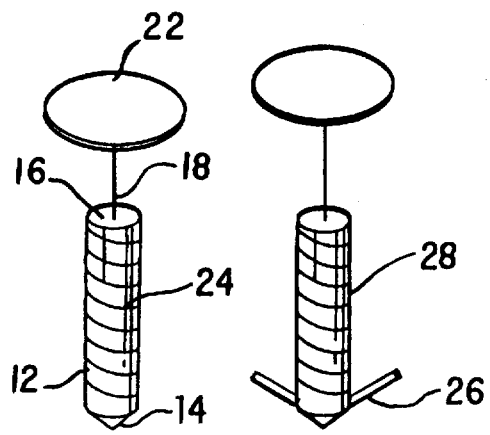
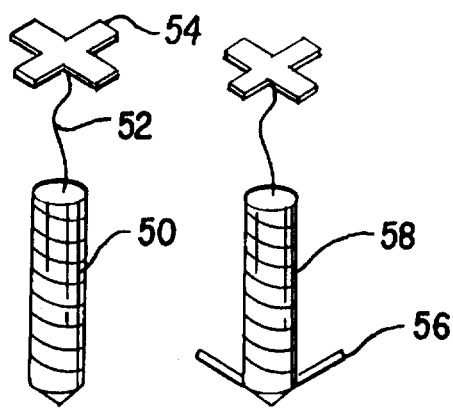
FIG. 2a   FIG. 2b   FIG. 5a   FIG. 5b
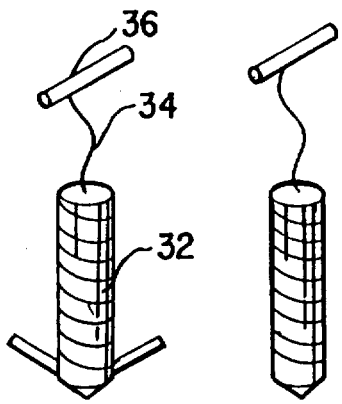
FIG. 3a   FIG. 3b
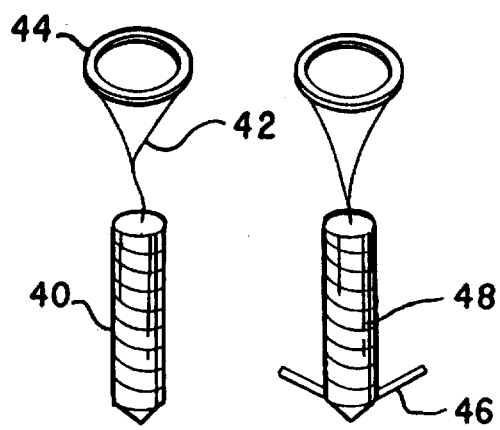
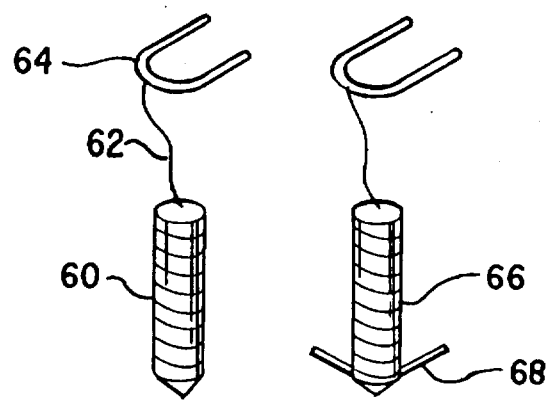
FIG. 4a   FIG. 4b   FIG. 6a   FIG. 6b

KNOTLESS SUTURE ANCHOR ASSEMBLY

This application is a continuation in part of prior U.S. application Ser. No. 08/471,508, filed Jun. 6, 1995, now U.S. Pat. No. 5,569,306.

BACKGROUND OF THE INVENTION

1. Field of the Invention

The present invention relates to devices or assemblies used in tissue repair. More particularly, the assembly enables the attachment together or repair of portions of biological tissue (i.e., tendons or ligaments) onto a bone surface.

2. Description of the Background Art

Soft tissues, such as tendons and ligaments, generally are attached to bone by small collagenous fibers. These connections are strong but permit the tendons and ligaments to be flexible. When a tissue is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunnelling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as protheses, to bone. A suture anchor is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

A primary object of the present invention is to provide a suture anchor assembly which is easy to use and install.

Another object of the present invention is to provide a suture anchor assembly which allows for secure attachment of soft tissue to bone without the use or requirement of tying a knot.

Still another object of the present invention is to provide a suture anchor assembly which is compact and allows a surgeon to easily guide the tissue into a bone anchoring sleeve to enhance the security of the repair.

Still another object of the present invention is to provide an anchor assembly which allows for passage through soft tissue in a singular fashion without the need for additional instrumentation for passing the suture separately through the soft tissue to be repaired.

SUMMARY OF THE INVENTION

In accordance with the above objects, the present invention is a knotless suture anchor assembly for attachment or reattachment of biological soft tissue to bone. The unique knotless suture anchor assembly can be a one-piece device or include a hollow anchoring sleeve which is installed into a bone mass. The knotless suture anchor assembly or the anchoring sleeve can have a closed pointed drill end or be totally cylindrical in shape. The hollow one-piece assembly or anchoring sleeve can be ribbed or threaded on its exterior for secure attachment to the bone or embody varying types of conventional anchor configurations to facilitate a strong bond with the bone mass. A number of prior patents disclose configurations for the exterior of a bone anchor which are within the contemplation of the invention for use as the anchoring means for the exterior of the hollow anchoring sleeve.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying exterior structures which may embody the anchoring sleeve portion of the invention. These patents disclose various means and mechanisms for anchoring a device to a bone mass thus preventing pull-out of the sleeve after insertion into bone.

Further, the hollow anchoring sleeve can contain a collar on the rear portion or rear side of the hollow anchoring sleeve to control the depth of sleeve insertion into the bone and prevent excessive insertion depth.

A key component of the knotless one-piece or two-piece suture anchor assembly is the spike or plug member which has on its first end a configuration which allows for easy puncturing of a soft tissue and on its second or other end a means for attachment of a suture material. The first end can be pointed or frustoconical in shape. The spike or plug can be ribbed, beaded, threaded or expandable on its exterior surface for secure mating with the interior wall section of the hollow anchoring sleeve or the bone directly. The suture material which is attached to the rear end of the spike or plug member has attached thereto a stop means for grabbing the tissue to be reattached to the bone mass. The stop means is produced or made from various materials and is attached to the spike or plug by a selected length of suture.

The spike or plug member, suture and stop means can be all produced of the same material (i.e., molded). This would obviate need for the second end of the spike or plug member to have means for attachment of the suture thereto.

In the two-piece configuration, the spike or plug member is inserted during an open or endoscopic procedure, or the like, through the soft tissue and its piercing or pointed end is then inserted into the anchoring sleeve to facilitate a secure mating. Once the spike or plug member is threaded through the tissue and is inserted into the hollow anchoring sleeve, it is then securely attached through pressure by the surgeon into the sleeve. This attachment of the spike member to the hollow anchoring sleeve can be accomplished in one step or in a number of depth control steps (i.e., ratchets) to fine tune the tightness of the repair. This ratchet effect can be accomplished by a series of beads, ribs, thickening or the like on the exterior of the spike component. These would mate with the interior of the anchor sleeve. This allows for the tissue to be tightly attached to the bone mass. The unique device obviates the need for the surgeon to tie a knot with the suture material for reattachment of tissue to bone. Endoscopic procedures and some open surgical procedures are extremely difficult and must be completed in a very tight space. Obviation of the need of tying a knot is extremely beneficial and innovative.

In addition, it is within the contemplation of this invention to produce a one-piece knotless suture anchor assembly that includes a spike or plug member which can act as the bone anchor and spike without the necessity of a hollow anchoring sleeve. The spike or plug member, suture and stop means are identical to that described above with the added feature of the spike or plug member having a bone anchoring means on its exterior surface.

The one-piece embodiment can be installed as described above. That is the spike or plug can be inserted through the soft tissue and then into the bone with the stop means grabbing the tissue and attaching or reattaching same to the bone mass. In the alternative, the stop means of the one-piece device can be inserted from the underside of the tissue mass through the mass, thereby obviating the need for the spike or plug with anchoring means from passing through the tissue. The spike or plug with anchor is then pressed into the bone mass pulling the tissue into attachment or reattachment to the bone mass.

As previously described, the suture and stop means can vary in shape and be produced of the same or different materials.

Numerous other features of various embodiments of the knotless suture anchor assembly will be apparent from the following detailed description and the accompanying drawings.

BRIEF DESCRIPTION OF THE DRAWINGS

FIGS. 2a and 2b are perspective views of a spike member with suture element and stop means made in accordance with the present invention;

FIGS. 3a and 3b are perspective views of an alternate embodiment of a spike member with suture element of the present invention;

FIGS. 4a and 4b are perspective views of an alternate embodiment of a spike member with suture element of the present invention;

FIGS. 5a and 5b are perspective views of an alternate embodiment of a spike member with suture element of the present invention;

FIGS. 6a and 6b are perspective views of an alternate embodiment of a spike member with suture element of the present invention;

FIG. 8 illustrates the procedure for attachment of tissue to bone mass for the embodiment as outlined in FIG. 2a;

DETAILED DESCRIPTION OF THE PRESENT INVENTION

Referring now to FIG. 1, the knotless two-piece suture anchor assembly of the present invention contains as one integral component a hollow anchoring sleeve for installation and attachment to a bone mass. The hollow anchoring sleeve 1, as shown in FIG. 1a, is cylindrical in shape and possesses ribs or threads on its exterior. The device can also contain or be configured with prongs, umbrella spokes, have threads, be expandable, or have wedges, on its exterior, for secure attachment with the bone mass. These exterior attachment features are known to the industry and incorporated herein by reference.

Figure 1D:
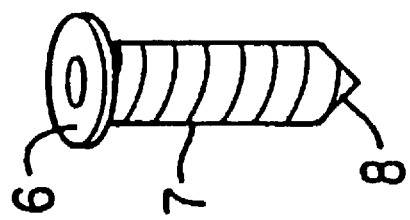
FIGS. 1a, 1b, 1c and 1d are perspective views of a hollow anchoring sleeve made in accordance with the present invention.
Figure 1C:
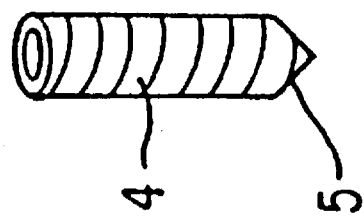
Figure 1B:
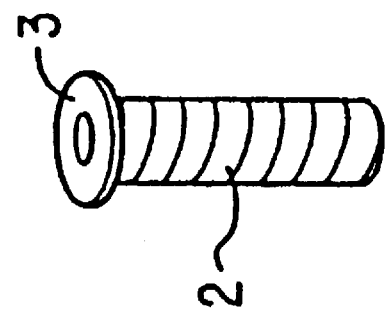
Figure 1A:
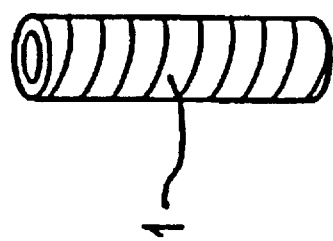

FIG. 1b illustrates an alternate embodiment of the hollow anchoring sleeve 2 having a collar 3 to control depth of bone penetration. The collar prevents the sleeve from being forced too deep into the bone mass when the spike or plug member is inserted.

FIG. 1c illustrates an alternate embodiment of the hollow anchoring sleeve 4 wherein the sleeve has a pointed closed end 5 for ease of penetration into a bone mass.

FIG. 1d illustrates a hollow anchoring sleeve 7 with a collar 6 and a closed pointed end 8 as an alternate construction.

As pointed out in the Summary of the Invention, the hollow anchoring sleeve may also be shaped or configured with any means to secure said structure to a bone mass. The hollow anchoring sleeve may include a threaded exterior as disclosed in U.S. Pat. No. 5,370,662, incorporated herein by reference. Further, the device may be expandable as disclosed in U.S. Pat. No. 5,084,050, incorporated herein by reference. A configuration such as disclosed in U.S. Pat. Nos. 5,037,422; 5,224,946; and 5,236,445 are also contemplated by the invention and these disclosures are incorporated by reference. Harpoon configurations such as disclosed in U.S. Pat. Nos. 5,141,520 and 5,102,421 are also contemplated for the hollow anchoring sleeve and incorporated herein by reference.

It is also within the contemplation of the present invention to configure the anchoring sleeve in a harpoon-type fashion such as disclosed by U.S. Pat. Nos. 4,632,101 and 4,721,103 for secure anchoring within the bone mass. U.S. Pat. Nos. 4,898,156; 5,207,679; 4,946,468; and 5,192,303 disclose anchoring mechanisms which can be utilized for the hollow sleeve member for installation within a bone mass. These patents are incorporated by reference and fall within the contemplation of the present invention for methods or means for anchoring the sleeve to the bone mass. It is also within the contemplation of the present invention to configure this dowel-like hollow sleeve in any fashion to securely attach same to a bone mass.

The interior surface of the hollow anchoring sleeve is ribbed, beaded, threaded, expandable or smooth for secure engagement with said exterior surface of said spike member.

FIG. 2, including 2a and 2b, shows a perspective view of the spike plug member with suture element and stop means, of the two-piece and one-piece embodiment, respectively, embodying the present invention. Spike or plug member 12 is preferably cylindrical in shape with a sharp first end 14 and a second end 16 wherein the suture element 18 is attached. The suture element 18 has at its distal end a disc-like stop means 22. The stop means 22 can be constructed of any material may be one molded component and attached to spike member 12 at end 16. Further, the suture element 18, alone, can be made from any type suture material which has been approved for surgical procedures or a molded material for attachment of tissue to bone. The spike or plug member can form any shape so long as it mates with the hollow cylindrical sleeve as described above. The exterior of the spike or plug member 12 may be ribbed or threaded 24 as depicted in FIG. 2 or may be beaded or expandable to allow for a secure tight fit with the inner hollow cylinder of the anchoring sleeve. Once inserted into a hollow anchoring sleeve, the exterior surface of the spike or plug member 12 engages the inner surface of the sleeve and can be ratcheted down to produce the desired tight fit. The interface of the spike and sleeve allows for movement of the spike in only one direction and resists pullout or movement out of the sleeve. This ratcheting effect allows for fine tuning and tightening of the soft tissue to the bone during repair. The length of the suture connection 18 is variable and may be adjusted prior to selection of a tool or during surgical procedure through any appropriate means. Likewise, the diameter of the disc-like stop means 22 is adjustable. FIG. 2b is identical to 2a but for anchoring means 6 attached to the spike or plug member 28. This one-piece embodiment allows for tissue reattachment without an anchoring sleeve. The spike or plug member anchors directly into the bone mass.

FIG. 3 illustrates an alternate embodiment of the spike member with suturing material and stop means. In FIG. 3a, the spike member 32 has attached at its rear a suture 34 and rod-like stop means 36. This is the embodiment of the one-piece anchor. FIG. 3b illustrates the spike or plug member of the two-piece embodiment when used in combination with an anchoring sleeve.

FIG. 4 illustrates an alternate embodiment of the spike member with suturing material and stop means. In FIG. 4a, the two-piece embodiment, Spike member 40 has attached thereto at least one suture means 42 connected to a stop means 44 configured in the shape of a ring or hoop. FIG. 4b illustrates the one-piece embodiment wherein anchoring means 46 is attached to the spike or plug member 48 for attachment to bone without an anchoring sleeve.

FIG. 5 contains alternate embodiments 5a and 5b. FIG. 5a, the two-piece embodiment, includes a spike means 50, a suture means 52 attached thereto, and an X-like stop means 54. FIG. 5b, the one-piece embodiment, illustrates an embodiment of the configuration wherein anchoring means 56 is attached to the spike or plug means 58 for attachment to bone when an anchoring sleeve is not utilized.

FIG. 6 contains FIGS. 6a and 6b which are alternate embodiments of the invention including a spike member 60, suturing means 62 attached thereto, and a stop means 64 configured in a horseshoe configuration. FIG. 6b illustrates an alternate embodiment of the horseshoe configuration wherein the spike or plug member 66 has anchoring means 68 attached thereon for direct attachment to bone without the utilization of an anchoring sleeve.

Figure 7:
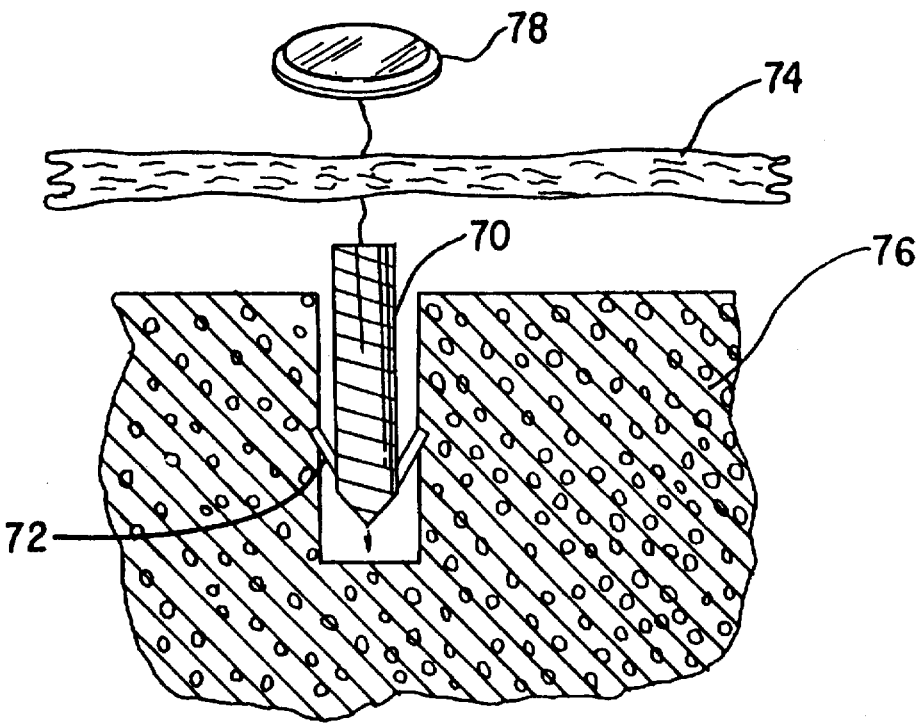
FIG. 7 illustrates the procedure for attachment of tissue to bone mass for the embodiment as outlined in FIG. 2b.
Figure 8:
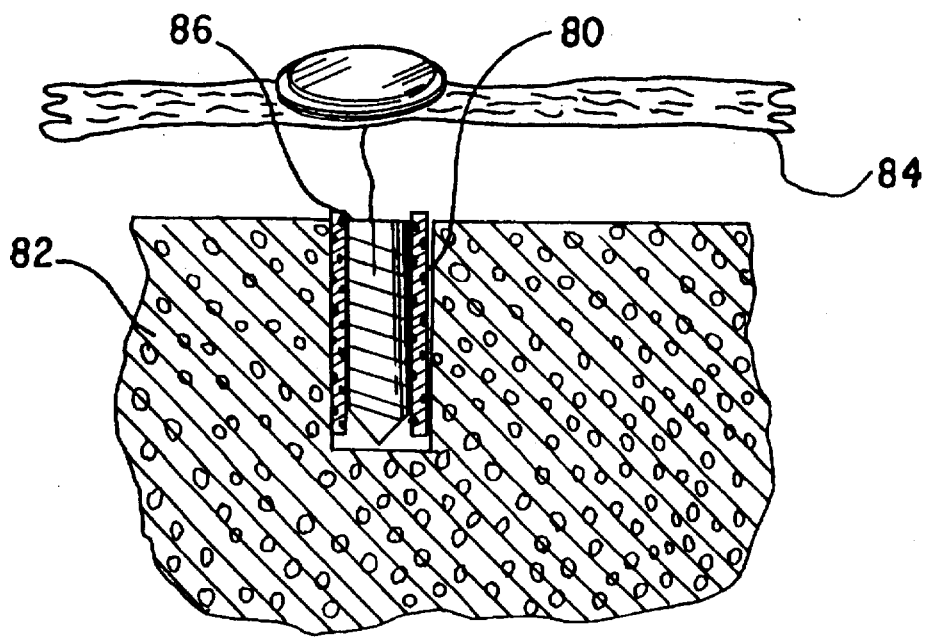

Referring now to FIG. 7 and FIG. 8, there is illustrated a surgical procedure for reattaching or attaching tissue to bone depicting the spike or plug embodiments illustrated in FIG. 2. The procedure can be enacted for any of the embodiments outlined in FIGS. 2, 3, 4, 5 and 6. FIG. 7 illustrates the procedure wherein an anchoring sleeve is not utilized. Spike or plug means 70 having anchoring means 72 is inserted through tissue 74 and directly into bone 76. The stop means 78 grabs the tissue 74 and pulls same back into reattachment or attachment with bone 76 when the spike or plug member is forced into the opening in the bone. The tightness of the repair is adjusted by the length of suture 70 and/or the depth of the insertion of spike member 72 into the bone mass.

FIG. 8 depicts a procedure wherein an anchoring sleeve 80 is first inserted into bone mass 82. Subsequent to the insertion of the anchoring sleeve 80, a spike or plug member 86 is inserted through tissue 84 and into the anchoring sleeve 80. The spike or plug member 86 is then ratcheted down into the anchoring sleeve 80 to pull tissue mass 84 into direct and secure mating with bone mass 82.

Figure 9:
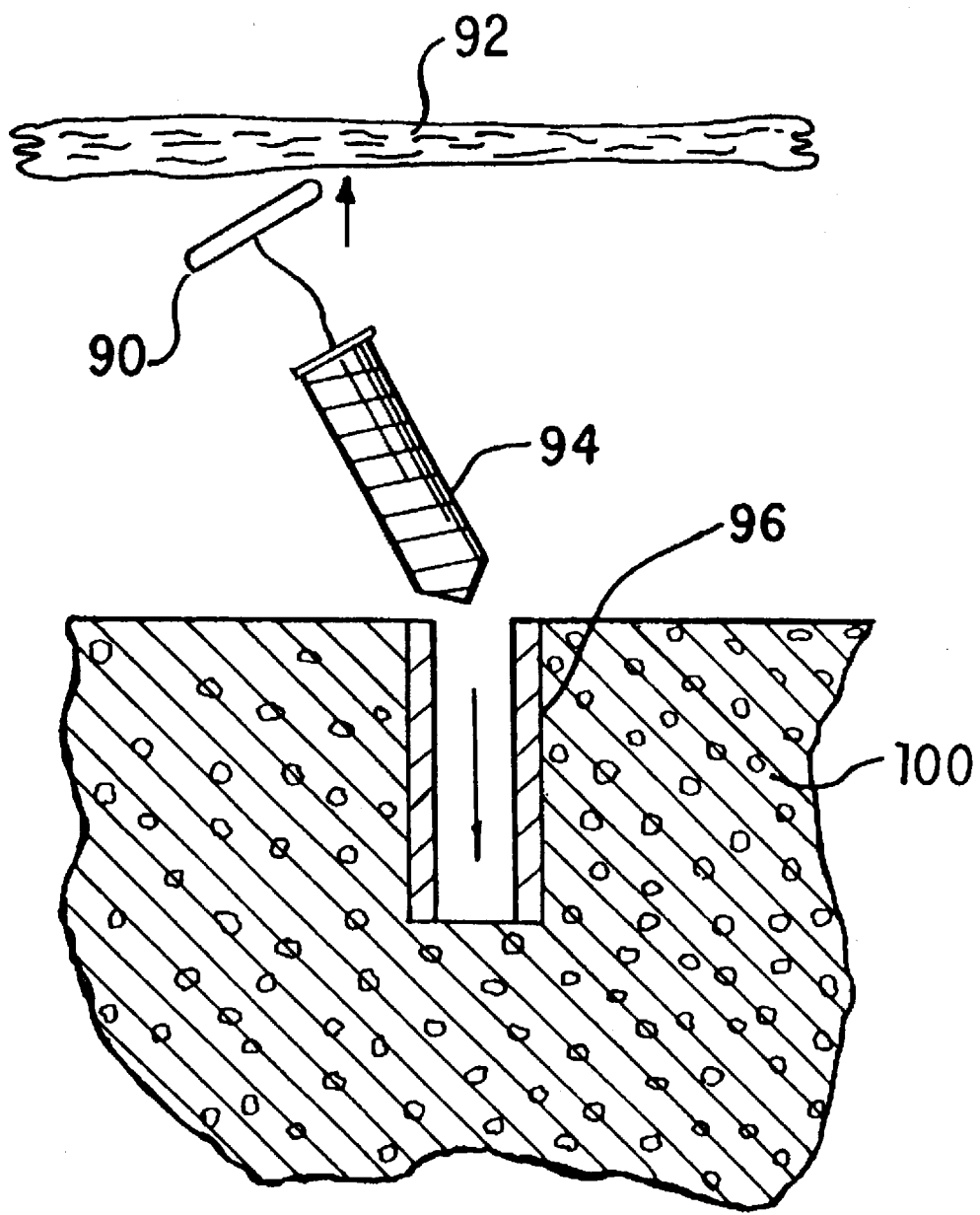
FIG. 9 illustrates one procedure for attachment of tissue to bone mass for the embodiment as outlined in FIG. 3b.

Referring now to FIG. 9, there is an alternate surgical procedure disclosed for utilization of the rod-like stop means depicted in FIG. 3. Initially the rod-like stop means 90 is inserted through tissue mass 92. Once the rod-like stop means rests on top of the tissue mass, the spike or plug member 94 is then inserted into a previously inserted anchoring sleeve 96. The spike or plug member 94 is then ratcheted down into the anchoring sleeve for secure mating or attachment of the tissue 92 to the bone mass 100. This procedure may also be undertaken with the one-piece anchor having a spike or plug means as depicted in FIG. 3a which omits the initial insertion of an anchoring sleeve.

Figure 10:
FIG. 10 is a perspective view of a spike member with a smooth exterior.
Figure 12:
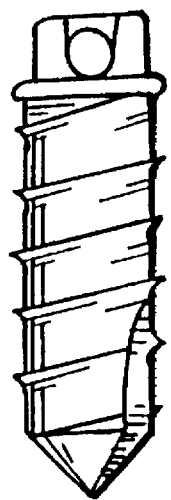
FIG. 12 is a perspective view of a spike member with a threaded exterior.
Figure 11:
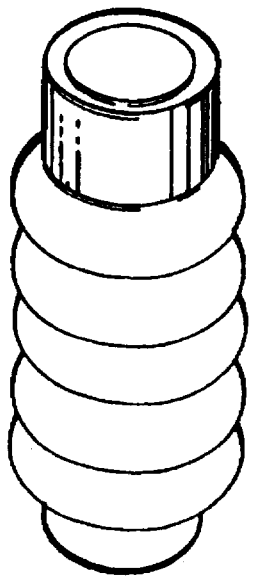
FIG. 11 is a perspective view of a spike member with a ribbed exterior.
Figure 13:
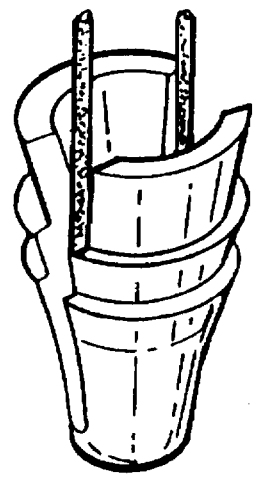
FIG. 13 is a perspective view of a spike member with an expandable exterior.

FIGS. 10–13 illustrate varying embodiments of the exterior surface of the spike member. FIG. 10 illustrates a spike with a smooth exterior, FIG. 11 illustrates a spike member with a ribbed exterior, FIG. 12 illustrates a spike member with a threaded exterior, and FIG. 13 illustrates a spike member with an expandable exterior.

Figure 15:
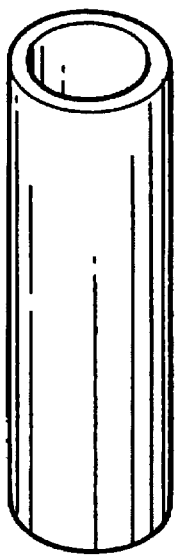
FIG. 15 with a smooth exterior.
Figure 14:
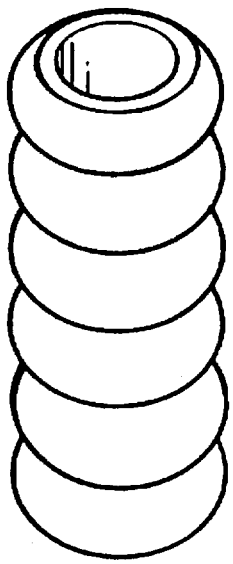
FIG. 14 is a perspective view of a hollow anchoring sleeve with a ribbed exterior.
Figure 16:
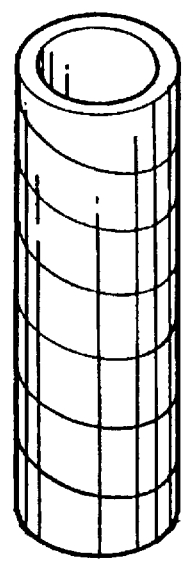
FIG. 16 with a threaded exterior.

FIGS. 14–16 illustrate embodiments for the exterior of the hollow anchoring sleeve member. FIG. 14 illustrates a ribbed exterior, FIG. 15 illustrates a smooth exterior and FIG. 16 illustrates a threaded exterior.

Figure 17:
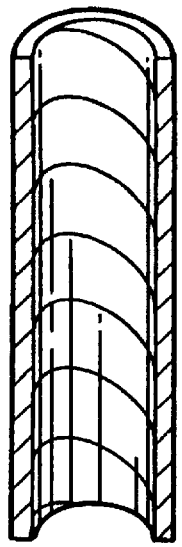
FIG. 17 is a cross-sectional view of a hollow anchoring sleeve with a threaded interior.
Figure 18:
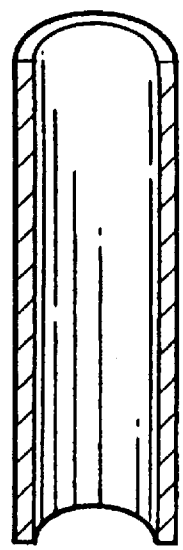
FIG. 18 with a smooth interior.
Figure 19:
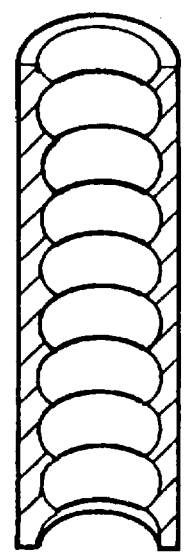
FIG. 19 with a ribbed interior.

FIGS. 17–19 illustrate alternate embodiments for the interior of the hollow anchoring sleeve. FIG. 17 illustrates a threaded interior, FIG. 18 illustrates a smooth interior and FIG. 19 illustrates a ribbed interior.

FIG. 10–19 are illustrative of varying embodiments of the invention and those reasonably skilled in the art could contemplate as part of this invention varying other embodiments for such surfaces.

In addition to the shapes illustrated for the stop or catch means portion of the invention, the stop means can be any planar or non-planar shape such as, but not limited to, C-shaped, planar with one or more openings, bar-shaped, curved or non-planar bar-shaped. Further the stop means is attached to the spike or plug member by one or more suture elements. The suture element or connection can be made up of a known suture material such as Ethibond® or Prolene®, or it can be made of polymer materials such as ultrahigh molecular weight polyethylene. The connection or suture element can be formed of bio-absorbable material such as a polylactide polymer. Additionally, the suture element can be part of the stop means and formed by a molding process or the like.

The suture element can be connected to the stop means and an anchor in a variety of ways such as fusion or molding or by mechanical means such as glue, a weld or by mere tieing.

In many situations throughout the discussion above, the terminology secure attachment of soft tissue to bone has been used. Such terminology refers to the attachment or reattachment of tissue to bone through the insertion of a spike member into a hollow anchoring sleeve or a spike/anchor means into a bone mass. In the former situation, the spike member can seat into the sleeve in a one step mating procedure or be inserted and ratcheted down in a step wise fashion into the sleeve. Either situation will function effectively and selection is based upon the instant facts of the surgical procedure. Further, the sleeve itself may be seated in the bone mass at varying depths. Again, such depth is a selection based upon the facts of the instant procedure. In the latter situation, where a spike/anchor means is used, depth of insertion of the device into the bone is a selection or choice of the surgeon during the procedure. In all situations, the spike member or spike/anchor means is designed not to back up or exit once mated with the sleeve, ratcheted down into the sleeve, or inserted into the bone mass to avoid and prevent withdrawal therefrom.

It is also within the contemplation of the invention to make the spike or plug member for direct insertion into the bone with screws, prongs, spikes, a wedge means or any means wherein the spike or plug member anchors securely into the bone mass facilitating attachment or reattachment of tissue to skin.

Further, the spike or plug member or a portion of the spike or plug member may be made with bioabsorbable material.

While a preferred embodiment of the invention in a knotless suture anchor system has been shown and described herein, it should be understood that the present disclosure is made by way of example only and that variations to the structure shown and its use are possible within the scope of this disclosure without departing from the subject matter coming within the scope of the following claims, and a reasonable equivalency thereof, which claims we regard as our invention.

What is claimed is:

1. A knotless suture anchor assembly for attachment of tissue to bone, said assembly comprising:
    a) a spike member having a first end and a second end;
    b) at least one suture element having a first end and a second end wherein said first end of said at least one suture element is connected to said second end of said spike member;
    c) a stop means connected to said second end of said suture element; and
    d) a hollow anchoring sleeve for installation and attachment to a bone mass for receiving and having a length sufficient to completely encircle said first end and said second end of said spike member.

2. A knotless suture anchor assembly as claimed in claim 1, wherein said spike member has an exterior surface which is smooth, ribbed, threaded, or expandable for secure engagement of said spike member with said hollow anchoring sleeve.

3. A knotless suture anchor assembly as claimed in claim 1, wherein said hollow anchoring sleeve has an exterior surface which is ribbed, threaded, for secure engagement of said sleeve with said bone mass.

4. A knotless suture anchor assembly as claimed in claim 1, wherein said hollow anchoring sleeve has an interior surface which is ribbed, threaded, or smooth for secure engagement of said spike member.

5. A knotless suture anchor assembly as claimed in claim 1, wherein said stop means is disc-shaped, rod-shaped, ring-shaped, x-shaped, or horseshoe-shaped.

6. A knotless suture anchor assembly as claimed in claim 1, wherein said hollow anchoring sleeve has a first end and a second end and a collar attached to said first end for secure engagement of said hollow anchoring sleeve with said bone mass.

7. A method for the attachment of tissue to a bone mass utilizing said assembly as claimed in claim 1, comprising the steps of:
    a) installing said hollow anchoring sleeve in said bone mass; and
    b) inserting said spike member through said tissue and then into said hollow anchoring sleeve.

8. A method for the attachment of tissue to bone utilizing the method as claimed in claim 7, further comprising the step of:
    c) ratcheting down said spike member into said hollow anchoring sleeve to a desired depth for secure attachment of said tissue to said bone mass.

9. A method for the attachment of tissue to a bone mass utilizing said assembly as claimed in claim 1, comprising the steps of:
    a) installing said hollow anchoring sleeve in said bone mass;
    b) inserting said stop means through an underside of said tissue mass; and
    c) inserting said spike member into said hollow anchoring sleeve.

10. A method for the attachment of tissue to bone utilizing the method as claimed in claim 9, further comprising the step of:
    d) ratcheting down said spike member into said hollow anchoring sleeve to a desired depth for secure attachment of said tissue to said bone mass.

11. A method for the attachment of tissue to a bone mass utilizing said assembly as claimed in claim 1, comprising the steps:
    a) inserting said stop means through an underside of said tissue mass; and
    b) inserting said spike member through said tissue and then into said hollow anchoring sleeve and then inserting the sleeve with the anchor therein into said bone mass.

12. A knotless suture anchor assembly for attachment of tissue to bone, said assembly comprising:

a) a spike member having a first end and a second end;

b) at least one suture element having a first end and a second end wherein said first end of said suture element is connected to said second end of said spike member;

c) a stop mean having a surface for securing said tissue and being permanently attached to said second end of said suture element; and d) an anchor means connected to said first end of said spike member for installation and attachment of said spike member to said bone mass.

13. A knotless suture anchor assembly as claimed in claim 12, wherein said stop means is disc-shaped, rod-shaped, ring-shaped, X-shaped, or horseshoe-shaped.

14. A method for the attachment of tissue to a bone mass utilizing said assembly as claimed in claim 12, comprising the steps of:

a) inserting said spike member through said tissue and then into said bone mass.

* * * * *